United States Patent
Rhodes

(10) Patent No.: US 11,197,450 B1
(45) Date of Patent: Dec. 14, 2021

(54) SOYBEAN CULTIVAR 2564372

(71) Applicant: Benson Hill Seeds, Inc., St. Louis, MO (US)

(72) Inventor: William K. Rhodes, Queenstown, MD (US)

(73) Assignee: Benson Hill Seeds, Inc., St. Louis, MO (US)

( * ) Notice: Subject to any disclaimer, the term of this patent is extended or adjusted under 35 U.S.C. 154(b) by 0 days.

(21) Appl. No.: 16/893,416

(22) Filed: Jun. 4, 2020

(51) Int. Cl.
*A01H 6/54* (2018.01)
*A01H 5/10* (2018.01)

(52) U.S. Cl.
CPC ............... *A01H 6/542* (2018.05); *A01H 5/10* (2013.01)

(58) Field of Classification Search
CPC ...................................................... A01H 6/542
See application file for complete search history.

(56) References Cited

U.S. PATENT DOCUMENTS

| | | | |
|---|---|---|---|
| 5,304,719 | A | 4/1994 | Segebart |
| 5,367,109 | A | 11/1994 | Segebart |
| 5,523,520 | A | 12/1996 | Hunsperger |
| 5,850,009 | A | 12/1998 | Kevern |
| 5,968,830 | A | 10/1999 | Dan et al. |
| 2013/0055462 | A1* | 2/2013 | Eby .......................... A01H 5/10 800/263 |

OTHER PUBLICATIONS

Eshed, Y., et al. (1996) Less-Than-Epistatic Interactions of Quantitative Trait Loci in Tomato. Genetics. 43:1807-1817.

Goldman, I.L., et al. (1994) Molecular Markers Associated with Maize Kernel Oil Concentration in an Illinois High Protein x Illinois Low Protein Cross. Crop Sci. 34:908-915.

Kraft, T., et al. (2000) Linkage disequilibrium and fingerprinting in sugar beet. Theor. Appl. Genet. 101:323-326.

Narvel, J.M., et al. (2001) A Retrospective DNA Marker Assessment of the Development of Insect Resistant Soybean. 41:1931-1939.

Poehlman, J.M., et al. Methods in Plant Breeding in Breeding Field Crops, 4th edition. (1995), Iowa State University Press. pp. 172-174.

Willmot, D.B., et al. (1989) Genetic Analysis of Brown Stem Rot Resistance in Soybean. Crop Sci. 29:672-674.

Freytag, A.H. et al. (1989) Somaclonal variation in soybean plants regenerated from tissue culture. Plant Cell Reports. 8(4):pp. 199-202.

* cited by examiner

*Primary Examiner* — David H Kruse
(74) *Attorney, Agent, or Firm* — Weatherly IP Solutions, LLC; Barbara Campbell

(57) ABSTRACT

A soybean cultivar designated 2564372 is disclosed. Embodiments include the seeds of soybean 2564372, the plants of soybean 2564372, to plant parts of soybean 2564372, and methods for producing a soybean plant produced by crossing soybean 2564372 with itself or with another soybean variety. Embodiments include methods for producing a soybean plant containing in its genetic material one or more genes or transgenes and the transgenic soybean plants and plant parts produced by those methods. Embodiments also relate to soybean cultivars, breeding cultivars, plant parts, and cells derived from soybean 2564372, methods for producing other soybean cultivars, lines or plant parts derived from soybean 2564372, and the soybean plants, varieties, and their parts derived from use of those methods. Embodiments further include hybrid soybean seeds, plants, and plant parts produced by crossing 2564372 with another soybean cultivar.

20 Claims, No Drawings

SOYBEAN CULTIVAR 2564372

BACKGROUND

All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Soybean, *Glycine max* (L.) Merr., is an important and valuable field crop. Thus, a continuing goal of soybean plant breeders is to develop stable, high yielding soybean cultivars that are agronomically sound. The reasons for this goal are to maximize the amount of grain produced on the land used and to supply food for both animals and humans. To accomplish this goal, the soybean breeder must select and develop soybean plants that have traits that result in superior cultivars.

The foregoing examples of the related art and limitations related therewith are intended to be illustrative and not exclusive. Other limitations of the related art will become apparent to those of skill in the art upon a reading of the specification.

SUMMARY

It is to be understood that the embodiments include a variety of different versions or embodiments, and this Summary is not meant to be limiting or all-inclusive. This Summary provides some general descriptions of some of the embodiments, but may also include some more specific descriptions of other embodiments.

An embodiment provides a soybean cultivar designated 2564372. Another embodiment relates to the seeds of soybean cultivar 2564372, to the plants of soybean cultivar 2564372 and to methods for producing a soybean plant produced by crossing soybean cultivar 2564372 with itself or another soybean cultivar, and the creation of variants by mutagenesis or transformation of soybean cultivar 2564372.

Any such methods using the soybean cultivar 2564372 are a further embodiment: selfing, backcrosses, hybrid production, crosses to populations, and the like. All plants produced using soybean cultivar 2564372 as at least one parent are within the scope of the embodiments. Advantageously, soybean cultivar 2564372 could be used in crosses with other, different soybean plants to produce first generation ($F_1$) soybean hybrid seeds and plants with superior characteristics.

Another embodiment provides for single or multiple gene converted plants of soybean cultivar 2564372. The transferred gene(s) may be a dominant or recessive allele. The transferred gene(s) may confer such traits as herbicide resistance, insect resistance, resistance for bacterial, fungal, or viral disease, male fertility, male sterility, enhanced nutritional quality, modified fatty acid metabolism, modified carbohydrate metabolism, modified seed yield, modified oil percent, modified protein percent, modified lodging resistance, modified shattering, modified iron-deficiency chlorosis, and industrial usage. The gene may be a naturally occurring soybean gene or a transgene introduced through genetic engineering techniques.

Another embodiment provides for regenerable cells for use in tissue culture of soybean cultivar 2564372. The tissue culture may be capable of regenerating plants having all the physiological and morphological characteristics of the foregoing soybean plant, and of regenerating plants having substantially the same genotype as the foregoing soybean plant. The regenerable cells in such tissue cultures may be embryos, protoplasts, meristematic cells, callus, pollen, leaves, ovules, anthers, cotyledons, hypocotyl, pistils, roots, root tips, flowers, seeds, petiole, pods, or stems. Still a further embodiment provides for soybean plants regenerated from the tissue cultures of soybean cultivar 2564372.

Another embodiment provides for a method of editing the genome of soybean cultivar plant 2564372, said method comprising editing the genome of the plant, or plant part thereof, of soybean cultivar 2564372, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system.

The soybean seed of soybean cultivar 2564372 may be provided as an essentially homogeneous population of soybean cultivar 2564372. Essentially homogeneous populations of seed are generally free from substantial numbers of other seed.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

As used herein, "sometime" means at some indefinite or indeterminate point of time. So for example, as used herein, "sometime after" means following, whether immediately following or at some indefinite or indeterminate point of time following the prior act.

Various embodiments are set forth in the Detailed Description as provided herein and as embodied by the claims. It should be understood, however, that this Summary does not contain all of the aspects and embodiments, is not meant to be limiting or restrictive in any manner, and that embodiment(s) as disclosed herein is/are understood by those of ordinary skill in the art to encompass obvious improvements and modifications thereto.

In addition to the exemplary aspects and embodiments described above, further aspects and embodiments will become apparent by study of the following descriptions.

DEFINITIONS

In the description and tables herein, a number of terms are used. In order to provide a clear and consistent understanding of the specification and claims, including the scope to be given such terms, the following definitions are provided:

Cotyledon. A cotyledon is a type of seed leaf. The cotyledon contains the food storage tissues of the seed.

Embryo. The embryo is the small plant contained within a mature seed.

$F_3$. The "$F_3$" symbol denotes a generation resulting from the selfing of the $F_2$ generation along with selection for type and rogueing of off-types. The "F" number is a term commonly used in genetics, and designates the number of the filial generation. The "F$_3$" generation denotes the offspring resulting from the selfing or self-mating of members of the generation having the next lower "F" number, that is, the "F$_2$" generation.

Gene. Gene refers to a segment of nucleic acid. A gene can be introduced into a genome of a species, whether from a different species or from the same species, using transformation, gene editing techniques, or various breeding methods.

Hilum. Hilum refers to the scar left on the seed that marks the place where the seed was attached to the pod prior to the seed being harvested.

Hypocotyl. A hypocotyl is the portion of an embryo or seedling between the cotyledons and the root. Therefore, it can be considered a transition zone between shoot and root.

Iron Deficiency Chlorosis. Iron deficiency chlorosis (IDC) is a yellowing of the leaves caused by a lack of iron in the soybean plant. Iron is essential in the formation of chlorophyll, which gives plants their green color. In high pH soils iron becomes insoluble and cannot be absorbed by plant roots. Soybean cultivars differ in their genetic ability to utilize the available iron. A score of 9 means no stunting of the plants or yellowing of the leaves and a score of 1 indicates the plants are dead or dying caused by iron deficiency, a score of 5 means plants have intermediate health with some leaf yellowing.

Linoleic Acid Percent. Linoleic acid is one of the five most abundant fatty acids in soybean seeds. It is measured by gas chromatography.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism, and modified protein metabolism. The trait may be, for example, conferred by a naturally occurring gene introduced into the genome of the variety by gene editing, backcrossing, a natural or induced mutation, or a transgene introduced through genetic transformation techniques. A locus may comprise one or more alleles integrated at a single chromosomal location.

Lodging Resistance. Lodging resistance refers to the relative presence of the plant lying on or toward the ground and is on a 1 to 5 scoring basis. A lodging score of 5 would indicate the plant is basically lying on the ground. A score of 1 indicates that most or all the plants in a row are standing prostrate.

Maturity Date. Plants are considered mature when 95% of the pods have reached their mature color. The number of days are calculated either from August 31 or from the planting date.

Maturity Group. Maturity group refers to an agreed-on industry division of groups of varieties based on zones in which they are adapted, primarily according to day length or latitude. They consist of very long day length varieties (Groups 000, 00, 0), and extend to very short-day length varieties (Groups VII, VIII, IX, X).

Oil or Oil Percent. Soybean seeds contain a considerable amount of oil. Oil is measured by NIR spectrophotometry and is reported as a percentage basis.

Oleic Acid Percent. Oleic acid is one of the five most abundant fatty acids in soybean seeds and is measured by gas chromatography and is reported as a percent of the total oil content.

Palmitic Acid Percent. Palmitic acid is one of the five most abundant fatty acids in soybean seeds and is measured by gas chromatography and is reported as a percent of the total oil content.

*Phytophthora* Tolerance. Tolerance to *Phytophthora* root rot is rated on a scale of 1 to 9, with a score of 9 being the best or highest tolerance ranging down to a score of 1 which indicates the plants have no tolerance to *Phytophthora*.

Plant. A plant refers to a whole plant, any part thereof, or a cell or tissue culture derived from a plant, comprising any of: whole plants, plant components or organs (e.g., leaves, stems, roots, etc.), plant tissues, seeds, embryos, plant cells, protoplasts and/or progeny of the same. A plant cell is a biological cell of a plant, taken from a plant or derived through culture of a cell taken from a plant.

Plant Height. Plant height is taken from the top of the soil to the top node of the plant and is measured in centimeters.

Plant Parts. Plant parts (or a soybean plant, or a part thereof) includes but is not limited to protoplasts, cells, leaves, stems, roots, root tips, anthers, pistils, seed, grain, embryo, pollen, ovules, cotyledon, hypocotyl, pod, flower, shoot, tissue, petiole, cells, meristematic cells, and the like.

Pod. Pod refers to the fruit of a soybean plant. It consists of the hull or shell (pericarp) and the soybean seeds.

Progeny. Progeny includes an F$_1$ soybean plant produced from the cross of two soybean plants where at least one plant includes soybean cultivar 2564372 and progeny further includes, but is not limited to, subsequent F$_2$, F$_3$, F$_4$, F$_5$, F$_6$, F$_7$, F$_8$, F$_9$, and F$_{10}$ generational crosses with the recurrent parental line.

Protein Percent. Soybean seeds contain a considerable amount of protein. Protein is generally measured by NIR spectrophotometry.

Pubescence. Pubescence refers to a covering of very fine hairs closely arranged on the leaves, stems, and pods of the soybean plant.

Relative Maturity (RM). The term relative maturity is a numerical value that is assigned to a soybean variety based on comparisons with the maturity values of other varieties. The number preceding the decimal point in the RM refers to the maturity group. The number following the decimal point refers to the relative earliness or lateness within each maturity group. For example, a 3.0 is an early group III variety, while a 3.9 is a late group III variety.

Seed Yield (Bushels/Acre). The yield in bushels/acre is the actual yield of the grain at harvest.

Seeds Per Pound. Soybean seeds vary in seed size; therefore, the number of seeds required to make up one pound also varies. The number of seeds per pound affects the pounds of seed required to plant a given area and can also impact end uses.

Single Gene Converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering. By essentially all of the morphological and physiological characteristics, it is meant that the characteristics of a plant are recovered that are otherwise present when compared in the same environment, other than an occasional variant trait that might arise during backcrossing or direct introduction of a transgene.

Sulfonylurea Reaction. Sulfonylurea reaction refers to a plant's tolerance, resistance or susceptibility to sulfonylurea herbicides and refers to a plant which contains the ALS gene, which confers resistance to some of the sulfonylurea herbicides.

Trypsin. Trypsin is a digestive enzyme, specifically, a pancreatic serine protease enzyme with substrate specificity based upon positively charged lysine and arginine side chains and is excreted by the pancreas. Trypsin aids in the digestion of food proteins and other biological processes.

Trypsin inhibitor units. Trypsin inhibitor units or abbreviated as TIU, is an assay measuring the quantity of trypsin inhibitor in a soybean seed or soybean product thereof. Measurement of trypsin inhibitor units is a technique well-known in the art.

DETAILED DESCRIPTION

Soybean cultivar 2564372 is a mid-group IV maturity variety. Additionally, soybean cultivar 2564372 is resistant to Soybean Cyst Nematode Race 3, is not tolerant to Sulfonylurea, and has the Rps 1c conferring resistance to *Phythophora* root rot.

Some of the selection criteria used for various generations include: seed yield, lodging resistance, emergence, disease tolerance, maturity, late season plant intactness, plant height, and shattering resistance.

Soybean cultivar 2564372 has shown uniformity and stability, as described in the following variety description information. Soybean cultivar 2564372 has been self-pollinated a sufficient number of generations with careful attention to uniformity of plant type and has been increased with continued observation for uniformity.

Soybean cultivar 2564372 has the following morphologic and other characteristics based primarily on data collected at the following locations: Marion, Ark.; Mascoutah, Ill.; Mt. Carmel, Ill.; Ridgway, Ill.; Wichita, Kans.; Vandalia, Ill.; Queenstown, Md.; Rock Hall, Md.; Matthews, Mo.; Crawfordsville, Ark.; DeWitt, Ark.; Greenville, Miss.; Proctor, Ark.; Iuka, Ill.; Linkwood, Md.; Charleston, Mo.; Pittsburgh, Mo.; Corning, Ark.; Wynne, Ark.; and Princeton, Ind.

TABLE 1

VARIETY DESCRIPTION INFORMATION

Hypocotyl Color: White
Seed Coat Color (Mature Seed): Clear

TABLE 1-continued

VARIETY DESCRIPTION INFORMATION

Seed Coat Luster (Mature Hand Shelled Seed): Dull
Seed Color (Mature Seed): Yellow
Leaflet Shape: Ovate
Growth Habit: Indeterminate
Flower Color: White
Hilum Color (Mature Seed): Black
Plant Pubescence Color: Light tawny
Pod Wall Color: Brown
Maturity Group: 4
Relative Maturity: 4.6
Plant Lodging Score: 2.3
Plant Height (cm): 94
Percent Protein: 43.54
Percent Oil: 19.4

Physiological Responses (known resistances/susceptibility): Resistant to Soybean Cyst Nematode Race 3, not tolerant to Sulfonylurea, and has the Rps 1c conferring resistance to Phythophora root rot In Table 2, the yield of soybean cultivar 2564372 is compared with the yield of soybean cultivars AG4632, AG4933, e4677, and N4757S between 2017 and 2019 in the United States in side-by-side trials. Column one shows the soybean cultivar designations, column two shows the year, column three shows the number of locations, column four shows the number of observations, and column five shows the yield in bushels per acre.

TABLE 2

Yield comparison with commercial cultivars

| Soybean Cultivar | Year | # of Locations | # of Observations | Yield |
|---|---|---|---|---|
| 2564372 | 2018-2019 | 15 | 15 | 58.7 |
| AG4632 | 2018-2019 | 15 | 15 | 58.2 |
| 2564372 | 2018-2019 | 15 | 15 | 59.2 |
| AG4933 | 2018-2019 | 15 | 15 | 57.4 |
| 2564372 | 2017 and 2019 | 15 | 15 | 60.6 |
| e4677 | 2017 and 2019 | 15 | 15 | 55.7 |
| 2564372 | 2017 and 2019 | 34 | 34 | 59.2 |
| N4757S | 2017 and 2019 | 34 | 34 | 60.6 |

In Table 3, the characteristics of soybean cultivar 2564372 are compared with soybean cultivars AG4632, AG4933, e4677, and N4757S.

TABLE 3

Comparison of characteristics with commercial cultivars

| Characteristic | Soybean Cultivar | | | | |
|---|---|---|---|---|---|
| | 2564372 | AG4632 | AG4933 | e4677 | N4757S |
| Flower color | White | Purple | Purple | White | Purple |
| Pubescence color | Light tawny | Light tawny | Gray | Tawny | Tawny |
| Hilum color | Black | Black | Imperfect black | Black | Black |
| Sulfonylurea reaction | Not tolerant | Tolerant | Not tolerant | Not tolerant | Tolerant |
| Soybean Cyst Nematode reaction | Resistant | Moderately resistant | Moderately resistant | Resistant | Resistant |
| Phytophthora reaction | Resistant - has the Rps 1c gene | Resistant - has the Rps 1a gene | Resistant - has the Rps 1c gene | Resistant - has the Rps 1c gene | |

Breeding With Soybean Cultivar 2564372

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

A population means a set comprising any number, including one, of individuals, objects, or data from which samples are taken for evaluation, e.g. estimating QTL effects and/or disease tolerance. Most commonly, the terms relate to a breeding population of plants from which members are selected and crossed to produce progeny in a breeding program. A population of plants can include the progeny of a single breeding cross or a plurality of breeding crosses and can be either actual plants or plant derived material, or in silico representations of plants. The member of a population need not be identical to the population members selected for use in subsequent cycles of analyses nor does it need to be identical to those population members ultimately selected to obtain a final progeny of plants. Often, a plant population is derived from a single biparental cross but can also derive from two or more crosses between the same or different parents. Although a population of plants can comprise any number of individuals, those of skill in the art will recognize that plant breeders commonly use population sizes ranging from one or two hundred individuals to several thousand, and that the highest performing 5% to 20% of a population is what is commonly selected to be used in subsequent crosses in order to improve the performance of subsequent generations of the population in a plant breeding program.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of soybean plant breeding is to develop new and superior soybean cultivars and hybrids. The breeder initially selects and crosses two or more parental lines, followed by repeated selfing and selection, producing many new genetic combinations. The breeder can theoretically generate billions of different genetic combinations via crossing, selection, selfing and mutations. Therefore, a breeder will never develop the same line, or even very similar lines, having the same soybean traits from the exact same parents.

Each year, the plant breeder selects the germplasm to advance to the next generation. This germplasm is grown under different geographical climate and soil conditions and further selections are then made during and at the end of the growing season. The cultivars that are developed are unpredictable because the breeder's selection occurs in environments with no control at the DNA level, and with millions of different possible genetic combinations being generated. A breeder of ordinary skill in the art cannot predict the final resulting lines he develops, except possibly in a very gross and general fashion. The same breeder cannot produce the same cultivar twice by using the same original parents and the same selection techniques. This unpredictability results in the expenditure of large amounts of research monies to develop superior new soybean cultivars.

The development of new soybean cultivars requires the development and selection of soybean varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines, as well as the phenotype of the hybrid, influence the breeder's decision whether to continue with the specific hybrid cross.

Breeding programs combine desirable traits from two or more cultivars or various broad-based sources into breeding pools from which cultivars are developed by selfing and selection of desired phenotypes. Pedigree breeding is used commonly for the improvement of self-pollinating crops. Two parents that possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

As used herein, "fertilization" and/or "crossing" broadly includes bringing the genomes of gametes together to form zygotes but also broadly may include pollination, syngamy, fecundation and other processes related to sexual reproduction. Typically, a cross and/or fertilization occurs after pollen is transferred from one flower to another, but those of ordinary skill in the art will understand that plant breeders can leverage their understanding of fertilization and the overlapping steps of crossing, pollination, syngamy, and fecundation to circumvent certain steps of the plant life cycle and yet achieve equivalent outcomes, for example, a plant or cell of a soybean cultivar described herein. In certain embodiments, a user of this innovation can generate a plant of the claimed invention by removing a genome from its host gamete cell before syngamy and inserting it into the nucleus of another cell. While this variation avoids the unnecessary steps of pollination and syngamy and produces a cell that may not satisfy certain definitions of a zygote, the process falls within the definition of fertilization and/or crossing as used herein when performed in conjunction with these teachings. In certain embodiments, the gametes are not different cell types (i.e. egg vs. sperm), but rather the same type and techniques are used to effect the combination of their genomes into a regenerable cell. Other embodiments of fertilization and/or crossing include circumstances where the gametes originate from the same parent plant, i.e. a "self" or "self-fertilization". While selfing a plant does not require the transfer pollen from one plant to another, those of skill in the art will recognize that it nevertheless serves as an example of a cross, just as it serves as a type of fertilization. Thus, methods and compositions taught herein are not limited to certain techniques or steps that must be performed to create a plant or an offspring plant of the claimed invention, but rather include broadly any method that is substantially the same and/or results in compositions of the claimed invention.

Crop Performance

Crop performance is used synonymously with plant performance and refers to of how well a plant grows under a set of environmental conditions and cultivation practices. Crop performance can be measured by any metric a user associates with a crop's productivity (e.g. yield), appearance and/or robustness (e.g. color, morphology, height, biomass, maturation rate), product quality (e.g., seed protein content, seed oil content, seed carbohydrate content, etc.), cost of goods sold (e.g. the cost of creating a seed, plant, or plant product in a commercial, research, or industrial setting) and/or a plant's tolerance to disease (e.g. a response associated with deliberate or spontaneous infection by a pathogen), pests, microbes, fungi, and/or environmental stress (e.g. drought, flooding, low nitrogen or other soil nutrients, wind, hail, temperature, day length, etc.). Crop performance can also be measured by determining a crop's commercial value and/or by determining the likelihood that a particular inbred, hybrid, or variety will become a commercial product, and/or by determining the likelihood that the offspring of an inbred, hybrid, or variety will become a commercial product. Crop performance can be a quantity (e.g. the volume or weight of seed or other plant product measured in liters or grams) or some other metric assigned to some aspect of a plant that can be represented on a scale (i.e., assigning a 1 to 10 value to a plant based on its disease tolerance).

A microbe will be understood to be a microorganism, i.e. a microscopic organism, which can be single celled or multicellular. Microorganisms are very diverse and include all the bacteria, archaea, protozoa, fungi, and algae, especially cells of plant pathogens and/or plant symbionts. Certain animals are also considered microbes, e.g. rotifers. In various embodiments, a microbe can be any of several different microscopic stages of a plant or animal. Microbes also include viruses, viroids, and prions, especially those which are pathogens or symbionts to crop plants.

A fungus includes any cell or tissue derived from a fungus, for example whole fungus, fungus components, organs, spores, hyphae, mycelium, and/or progeny of the same. A fungus cell is a biological cell of a fungus, taken from a fungus or derived through culture of a cell taken from a fungus.

A pest is any organism that can affect the performance of a plant in an undesirable way. Common pests include microbes, animals (e.g. insects and other herbivores), and/or plants (e.g. weeds). Thus, a pesticide is any substance that reduces the survivability and/or reproduction of a pest, e.g. fungicides, bactericides, insecticides, herbicides, and other toxins.

Tolerance or improved tolerance in a plant to disease conditions (e.g. growing in the presence of a pest) will be understood to mean an indication that the plant is less affected by the presence of pests and/or disease conditions with respect to yield, survivability and/or other relevant agronomic measures, compared to a less tolerant, more "susceptible" plant. Tolerance is a relative term, indicating that a "tolerant" plant survives and/or performs better in the presence of pests and/or disease conditions compared to other (less tolerant) plants (e.g., a different soybean cultivar) grown in similar circumstances. As used in the art, tolerance is sometimes used interchangeably with "resistance", although resistance is sometimes used to indicate that a plant appears maximally tolerant to, or unaffected by, the presence of disease conditions. Plant breeders of ordinary skill in the art will appreciate that plant tolerance levels vary widely, often representing a spectrum of more-tolerant or less-tolerant phenotypes, and are thus trained to determine the relative tolerance of different plants, plant lines or plant families and recognize the phenotypic gradations of tolerance.

Desired Trait or Traits

In certain embodiments, plants disclosed herein can be modified to exhibit at least one desired trait, and/or combinations thereof. The embodiments disclosed herein, are not limited to any set of traits that can be considered desirable, but nonlimiting examples include male sterility, herbicide tolerance, pest tolerance, disease tolerance, modified fatty acid metabolism, modified carbohydrate metabolism, modified seed yield, modified seed oil, modified seed protein, modified lodging resistance, modified shattering, modified iron-deficiency chlorosis, modified water use efficiency, and/or combinations thereof. Desired traits can also include traits that are deleterious to plant performance, for example, when a researcher desires that a plant exhibits such a trait in order to study its effects on plant performance.

Methods disclosed herein include conferring desired traits to plants, for example, by mutating sequences of a plant, introducing nucleic acids into plants, using plant breeding techniques and various crossing schemes, etc. These methods are not limited as to certain mechanisms of how the plant exhibits and/or expresses the desired trait. In certain nonlimiting embodiments, the trait is conferred to the plant by introducing a nucleotide sequence (e.g. using plant transformation methods) that encodes production of a certain protein by the plant. In certain nonlimiting embodiments, the desired trait is conferred to a plant by causing a null mutation in the plant's genome (e.g. when the desired trait is reduced expression or no expression of a certain trait). In certain nonlimiting embodiments, the desired trait is conferred to a plant by crossing two plants to create offspring that express the desired trait. It is expected that users of these teachings will employ a broad range of techniques and mechanisms known to bring about the expression of a desired trait in a plant. Thus, as used herein, conferring a desired trait to a plant is meant to include any process that causes a plant to exhibit a desired trait, regardless of the specific techniques employed.

Using Soybean Cultivar 2564372 to Develop Other Soybean Varieties

Soybean varieties such as soybean cultivar 2564372 are typically developed for use in seed and grain production. However, soybean varieties such as soybean cultivar 2564372 also provide a source of breeding material that may be used to develop new soybean varieties. Plant breeding techniques known in the art and used in a soybean plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of soybean varieties in a plant breeding program requires, in general, the development and evaluation of homozygous varieties. There are many analytical methods available to evaluate a new variety.

The oldest and most traditional method of analysis is the observation of phenotypic traits, but genotypic analysis may also be used.

Additional Breeding Methods

One embodiment is directed to methods for producing a soybean plant by crossing a first parent soybean plant with a second parent soybean plant, wherein the first or second soybean plant is the soybean plant from soybean cultivar 2564372. Further, both first and second parent soybean plants may be from soybean cultivar 2564372. Therefore, any methods using soybean cultivar 2564372 are part of the embodiments: selfing, backcrosses, hybrid breeding, and crosses to populations. Any plants produced using soybean cultivar 2564372 as at least one parent are also within the scope of the embodiments. Any such methods using soybean variety 2564372 are part of the embodiments: selfing, sibbing, backcrosses, mass selection, pedigree breeding, bulk selection, hybrid production, crosses to populations, and the like. These methods are well known in the art and some of the more commonly used breeding methods are described herein. Descriptions of breeding methods can be found in one of several reference books (e.g., Allard, Principles of Plant Breeding (1960); Simmonds, Principles of Crop Improvement (1979); Sneep, et al. (1979); Fehr, "Breeding Methods for Cultivar Development," Chapter 7, Soybean Improvement, Production and Uses, $2^{nd}$ ed., Wilcox editor (1987)).

The following describes breeding methods that may be used with soybean cultivar 2564372 in the development of further soybean plants. One such embodiment is a method for developing a cultivar 2564372 progeny soybean plant in a soybean plant breeding program comprising: obtaining the soybean plant, or a part thereof, of cultivar 2564372, utilizing said plant, or plant part, as a source of breeding material, and selecting a soybean cultivar 2564372 progeny plant with molecular markers in common with cultivar 2564372 and/or with morphological and/or physiological characteristics selected from the characteristics listed in Tables 1 and/or 2 and/or 3 and/or 4. Breeding steps that may be used in the soybean plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of soybean cultivar 2564372 progeny soybean plants, comprising crossing cultivar 2564372 with another soybean plant, thereby producing a population of soybean plants which, on average, derive 50% of their alleles from soybean cultivar 2564372. A plant of this population may be selected and repeatedly selfed or sibbed with a soybean cultivar resulting from these successive filial generations. One embodiment is the soybean cultivar produced by this method and that has obtained at least 50% of its alleles from soybean cultivar 2564372.

One of ordinary skill in the art of plant breeding would know how to evaluate the traits of two plant varieties to determine if there is no significant difference between the two traits expressed by those varieties. For example, see, Fehr and Walt, Principles of Cultivar Development, pp. 261-286 (1987). Thus, embodiments include soybean cultivar 2564372 progeny soybean plants comprising a combination of at least two cultivar 2564372 traits selected from the group consisting of those listed in Tables 1 and/or 2 and/or 3 and/or 4 or soybean cultivar 2564372 combination of traits listed in the Summary, so that said progeny soybean plant is not significantly different for said traits than soybean cultivar 2564372 as determined at the 5% significance level when grown in the same environmental conditions. Using techniques described herein, molecular markers may be used to identify said progeny plant as a soybean cultivar 2564372 progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of soybean cultivar 2564372 may also be characterized through their filial relationship with soybean cultivar 2564372, as for example, being within a certain number of breeding crosses of soybean cultivar 2564372. A breeding cross is a cross made to introduce new genetics into the progeny, and is distinguished from a cross, such as a self or a sib cross, made to select among existing genetic alleles. The lower the number of breeding crosses in the pedigree, the closer the relationship between soybean cultivar 2564372 and its progeny. For example, progeny produced by the methods described herein may be within 1, 2, 3, 4, or 5 breeding crosses of soybean cultivar 2564372.

Pedigree Breeding

Pedigree breeding starts with the crossing of two genotypes, such as soybean cultivar 2564372 and another soybean variety having one or more desirable characteristics that is lacking or which complements soybean cultivar 2564372. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically, in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous cultivar or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a soybean variety may be crossed with another variety to produce a first-generation progeny plant. The first-generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new soybean varieties.

Therefore, an embodiment is a method of making a backcross conversion of soybean variety 2564372, comprising the steps of crossing a plant of soybean variety 2564372 with a donor plant comprising a desired trait, selecting an $F_1$ progeny plant comprising the desired trait, and backcrossing the selected $F_1$ progeny plant to a plant of soybean variety 2564372. This method may further comprise the step of obtaining a molecular marker profile of soybean variety 2564372 and using the molecular marker profile to select for a progeny plant with the desired trait and the molecular marker profile of soybean cultivar 2564372. In one embodiment, the desired trait is a mutant gene, gene, or transgene present in the donor parent.

Recurrent Selection and Mass Selection

Recurrent selection is a method used in a plant breeding program to improve a population of plants. Soybean cultivar 2564372 is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating crops. A genetically variable population of heterozygous individuals is either identified, or created, by intercrossing several different parents. The plants are selected based on individual superiority, outstanding progeny, or excellent combining ability. The selected plants are intercrossed to produce a new population in which further cycles of selection are continued.

Single-Seed Descent

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Multiple-Seed Procedure

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population in each generation of inbreeding. Enough seeds are harvested to make up for those plants that did not germinate or produce seed.

Mutation Breeding

Mutation breeding is another method of introducing new traits into soybean variety 2564372. As used herein, a "mutation" is any change in a nucleic acid sequence. Non-limiting examples comprise insertions, deletions, duplications, substitutions, inversions, and translocations of any nucleic acid sequence, regardless of how the mutation is brought about and regardless of how or whether the mutation alters the functions or interactions of the nucleic acid. For example and without limitation, a mutation may produce altered enzymatic activity of a ribozyme, altered base pairing between nucleic acids (e.g. RNA interference interactions, DNA-RNA binding, etc.), altered mRNA folding stability, and/or how a nucleic acid interacts with polypeptides (e.g. DNA-transcription factor interactions, RNA-ribosome interactions, gRNA-endonuclease reactions, etc.). A mutation might result in the production of proteins with altered amino acid sequences (e.g. missense mutations, nonsense mutations, frameshift mutations, etc.) and/or the production of proteins with the same amino acid sequence (e.g. silent mutations). Certain synonymous mutations may create no observed change in the plant while others that encode for an identical protein sequence nevertheless result in an altered plant phenotype (e.g. due to codon usage bias, altered secondary protein structures, etc.). Mutations may occur within coding regions (e.g., open reading frames) or outside of coding regions (e.g., within promoters, terminators, untranslated elements, or enhancers), and may affect, for example and without limitation, gene expression levels, gene expression profiles, protein sequences, and/or sequences encoding RNA elements such as tRNAs, ribozymes, ribosome components, and microRNAs.

Methods disclosed herein are not limited to mutations made in the genomic DNA of the plant nucleus. For example, in certain embodiments a mutation is created in the genomic DNA of an organelle (e.g. a plastid and/or a mitochondrion). In certain embodiments, a mutation is created in extrachromosomal nucleic acids (including RNA) of the plant, cell, or organelle of a plant. Nonlimiting examples include creating mutations in supernumerary chromosomes (e.g. B chromosomes), plasmids, and/or vector constructs used to deliver nucleic acids to a plant. It is anticipated that new nucleic acid forms will be developed and yet fall within the scope of the claimed invention when used with the teachings described herein.

Methods disclosed herein are not limited to certain techniques of mutagenesis. Any method of creating a change in a nucleic acid of a plant can be used in conjunction with the disclosed invention, including the use of chemical mutagens (e.g. methanesulfonate, sodium azide, aminopurine, etc.), genome/gene editing techniques (e.g. CRISPR-like technologies, TALENs, zinc finger nucleases, and meganucleases), ionizing radiation (e.g. ultraviolet and/or gamma rays) temperature alterations, long-term seed storage, tissue culture conditions, targeting induced local lesions in a genome, sequence-targeted and/or random recombinases, etc. It is anticipated that new methods of creating a mutation in a nucleic acid of a plant will be developed and yet fall within the scope of the claimed invention when used with the teachings described herein.

Similarly, the embodiments disclosed herein are not limited to certain methods of introducing nucleic acids into a plant and are not limited to certain forms or structures that the introduced nucleic acids take. Any method of transforming a cell of a plant described herein with nucleic acids are also incorporated into the teachings of this innovation, and one of ordinary skill in the art will realize that the use of particle bombardment (e.g. using a gene-gun), *Agrobacterium* infection and/or infection by other bacterial species capable of transferring DNA into plants (e.g., *Ochrobactrum* sp., *Ensifer* sp., *Rhizobium* sp.), viral infection, and other techniques can be used to deliver nucleic acid sequences into a plant described herein. Methods disclosed herein are not limited to any size of nucleic acid sequences that are introduced, and thus one could introduce a nucleic acid comprising a single nucleotide (e.g. an insertion) into a nucleic acid of the plant and still be within the teachings described herein. Nucleic acids introduced in substantially any useful form, for example, on supernumerary chromosomes (e.g. B chromosomes), plasmids, vector constructs, additional genomic chromosomes (e.g. substitution lines), and other forms is also anticipated. It is envisioned that new methods of introducing nucleic acids into plants and new forms or structures of nucleic acids will be discovered and yet fall within the scope of the claimed invention when used with the teachings described herein.

Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, "Principles of Cultivar Development," Macmillan Publishing Company (1993). In addition, mutations created in other soybean plants may be used to produce a backcross conversion of soybean cultivar 2564372 that comprises such mutation.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the embodiments are intended to be within the scope of the embodiments.

Gene Editing Using CRISPR

Targeted gene editing can be done using CRISPR/Cas9 technology (Saunders & Joung, *Nature Biotechnology*, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system, including soybean. See for example, Liu, J., et al. Genome Editing in Soybean with CRISPR/Cas9. *Methods Mol Biol.* 2019. 1917:217-234.

Gene editing can also be done using crRNA-guided surveillance systems for gene editing. Additional information about crRNA-guided surveillance complex systems for gene editing can be found in the following documents: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476.

Therefore, it is another embodiment to use the CRISPR system on soybean cultivar 2564372 to modify traits and resistances or tolerances to pests, herbicides, and viruses.

Gene Editing Using TALENs

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing using soybean cultivar 2564372. The technique is well known in the art; see for example Malzahn, Aimee et al. "Plant genome editing with TALEN and CRISPR" *Cell & bioscience* vol. 7 21. 24 Apr. 2017.

Therefore, it is another embodiment to use the TALENs system on soybean cultivar to modify traits and resistances or tolerances to pests, herbicides, and viruses.

Other Methods of Genome Editing

In addition to CRISPR and TALENs, two other types of engineered nucleases can be used for genome editing: engineered homing endonucleases/meganucleases (EMNs), and zinc finger nucleases (ZFNs). These methods are well known in the art. See for example, Petilino, Joseph F.

"Genome editing in plants via designed zinc finger nucleases" *In Vitro Cell Dev Biol* Plant. 51(1): pp. 1-8 (2015); and Daboussi, Fayza, et al. "Engineering Meganuclease for Precise Plant Genome Modification" in Advances in New Technology for Targeted Modification of Plant Genomes. Springer Science+Business. pp 21-38 (2015).

Therefore, it is another embodiment to use engineered nucleases on soybean cultivar to modify traits and resistances or tolerances to pests, herbicides, and viruses.

Single-Gene Conversions

When the term "soybean plant" is used in the context of an embodiment, this also includes any single gene conversions of that variety. The term single gene converted plant as used herein refers to those soybean plants which are developed by a plant breeding technique called backcrossing wherein essentially all of the desired morphological and physiological characteristics of a variety are recovered in addition to the single gene transferred into the variety via the backcrossing technique. Backcrossing methods can be used with one embodiment to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental soybean plant that contributes the gene for the desired characteristic is termed the nonrecurrent or donor parent. This terminology refers to the fact that the nonrecurrent parent is used one time in the backcross protocol and therefore does not recur. The parental soybean plant to which the gene or genes from the nonrecurrent parent are transferred is known as the recurrent parent as it is used for several rounds in the backcrossing protocol (Poehlman & Sleper (1994); Fehr, Principles of Cultivar Development, pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic. Examples of these traits include, but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus. Several of these single gene traits are described in U.S. Pat. Nos. 5,959,185, 5,973,234, and 5,977,445, the disclosures of which are specifically hereby incorporated by reference.

Introduction of a New Trait or Locus into Soybean Cultivar 2564372

Variety 2564372 represents a new variety into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of Soybean Cultivar 2564372

A backcross conversion of soybean cultivar 2564372 occurs when DNA sequences are introduced through backcrossing (Hallauer, et al., "Corn Breeding," Corn and Corn Improvements, No. 18, pp. 463-481 (1988)), with soybean cultivar 2564372 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, Proceedings Symposium of the Analysis of Molecular Data, Crop Science Society of America, Corvallis, Oreg. (August 1994), where it is demonstrated that a backcross conversion can be made in as few as two backcrosses. In one embodiment, a breeder can combine the teachings herein with high-density molecular marker profiles spanning substantially the entire soybean genome to estimate the value of selecting certain candidates in a breeding program in a process commonly known as genome selection.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. (See, Hallauer, et al., Corn and Corn Improvement, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal, or viral), insect resistance, and herbicide resistance. In addition, an introgression site itself, such as an FRT site, Lox site, or other site-specific integration site, may be inserted by backcrossing and utilized for direct insertion of one or more genes of interest into a specific plant variety. In some embodiments, the number of loci that may be backcrossed into soybean cultivar 2564372 is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site-specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, Breeding Field Crops, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in soybean variety 2564372 comprises crossing soybean cultivar 2564372 plants grown from soybean cultivar 2564372 seed with plants of another soybean variety that comprise the desired trait or locus, selecting $F_1$ progeny plants that comprise the desired trait or locus to produce selected $F_1$ progeny plants, crossing the selected progeny plants with the soybean cultivar 2564372 plants to produce backcross progeny plants, selecting for backcross progeny plants that have the desired trait or locus and the morphological characteristics of soybean variety 2564372 to produce selected backcross progeny plants, and backcrossing to soybean cultivar 2564372 three or more times in succession to produce selected fourth or higher backcross progeny plants that comprise said trait or locus. The modified soybean cultivar 2564372 may be further characterized as having the physiological and morphological characteristics of soybean variety 2564372 listed in Table 1 as determined at the 5% significance level when grown in the same environmental conditions and/or may be characterized by percent similarity or identity to soybean cultivar 2564372 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny soybean seed by adding a step at the end of the process that comprises crossing soybean cultivar 2564372 with the introgressed trait or locus with a different soybean plant and harvesting the resultant first-generation progeny soybean seed.

Molecular Techniques Using Soybean Cultivar 2564372

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to "alter" (the utilization of up-regulation, down-regulation, or gene silencing) the traits of a plant in a specific manner. Any DNA sequences, whether from a different species or from the same species, which are introduced into the genome using transformation or various breeding methods are referred to herein collectively as "transgenes." In some embodiments, a transgenic variant of soybean cultivar 2564372 may contain at least one transgene but could contain at least 1, 2, 3, 4, 5, 6, 7, 8, 9, 10, and/or no more than 15, 14, 13, 12, 11, 10, 9, 8, 7, 6, 5, 4, 3, or 2. Over the last fifteen to twenty years several methods for producing transgenic plants have been developed, and another embodiment also relates to transgenic variants of the claimed soybean variety 2564372.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the embodiments may be produced by any means, including genomic preparations, cDNA preparations, in-vitro synthesis, RT-PCR, and in vitro or in vivo transcription.

One embodiment is a process for producing soybean variety 2564372 further comprising a desired trait, said process comprising introducing a transgene that confers a desired trait to a soybean plant of variety 2564372. Another embodiment is the product produced by this process. In one embodiment, the desired trait may be one or more of herbicide resistance, insect resistance, disease resistance, decreased phytate, or modified fatty acid or carbohydrate metabolism. The specific gene may be any known in the art or listed herein, including: a polynucleotide conferring resistance to imidazolinone, dicamba, sulfonylurea, glyphosate, glufosinate, triazine, PPO-inhibitor herbicides, benzonitrile, cyclohexanedione, phenoxy proprionic acid, and L-phosphinothricin; a polynucleotide encoding a *Bacillus thuringiensis* polypeptide; a polynucleotide encoding phytase, FAD-2, FAD-3, galactinol synthase, or a raffinose synthetic enzyme; or a polynucleotide conferring resistance to soybean cyst nematode, brown stem rot, *Phytophthora* root rot, soybean mosaic virus, or sudden death syndrome.

Numerous methods for plant transformation have been developed, including biological and physical plant transformation protocols. See, for example, Miki et al., "Procedures for Introducing Foreign DNA into Plants," in Methods in Plant Molecular Biology and Biotechnology, Glick and Thompson Eds., CRC Press, Inc., Boca Raton, pp. 67-88 (1993), and Armstrong, "The First Decade of Maize Transformation: A Review and Future Perspective," Maydica, 44:101-109 (1999). In addition, expression vectors and in vitro culture methods for plant cell or tissue transformation and regeneration of plants are available. See, for example, Gruber, et al., "Vectors for Plant Transformation," in Methods in Plant Molecular Biology and Biotechnology, Glick and Thompson Eds., CRC Press, Inc., Boca Raton, pp. 89-119 (1993).

A genetic trait which has been engineered into the genome of a particular soybean plant may then be moved into the genome of another variety using traditional breeding techniques that are well known in the plant breeding arts. For example, a backcrossing approach is commonly used to move a transgene from a transformed soybean variety into an already developed soybean variety, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing soybean cultivar 2564372.

Isozyme Electrophoresis and RFLPs have been widely used to determine genetic composition. Shoemaker and Olsen, Molecular Linkage Map of Soybean (*Glycine max* L. Men.), pp. 6.131-6.138 (1993). In S. J. O'Brien (ed.), Genetic Maps: Locus Maps of Complex Genomes, Cold Spring Harbor Laboratory Press, Cold Spring Harbor, N.Y., developed a molecular genetic linkage map that consisted of 25 linkage groups with about 365 RFLP, 11 RAPD (random amplified polymorphic DNA), 3 classical markers, and 4 isozyme loci. See also, Shoemaker, R. C., 1994 RFLP Map of Soybean, pp. 299-309; In R. L. Phillips and I. K. Vasil (ed.), DNA-based markers in plants, Kluwer Academic Press Dordrecht, the Netherlands.

SSR technology is currently the most efficient and practical marker technology. More marker loci can be routinely used, and more alleles per marker locus can be found, using SSRs in comparison to RFLPs. For example, Diwan and Cregan described highly polymorphic microsatellite loci in soybean with as many as 26 alleles. (Diwan, N., and Cregan. P. B., Automated sizing of fluorescent-labeled simple sequence repeat (SSR) markers to assay genetic variation in Soybean, *Theor. Appl. Genet.*, 95:220-225 (1997)). Single Nucleotide Polymorphisms may also be used to identify the unique genetic composition of the embodiment(s) and progeny varieties retaining that unique genetic composition. Various molecular marker techniques may be used in combination to enhance overall resolution.

Soybean DNA molecular marker linkage maps have been rapidly constructed and widely implemented in genetic studies. One such study is described in Cregan, et. al, "An Integrated Genetic Linkage Map of the Soybean Genome," *Crop Science*, 39:1464-1490 (1999). Sequences and PCR conditions of SSR Loci in Soybean, as well as the most current genetic map, may be found in Soybase on the World Wide Web.

Quantitative trait loci (QTL) refer to genetic loci that control to some degree numerically representable traits that are usually continuously distributed. One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a soybean plant for which soybean cultivar 2564372 is a parent can be used to produce double haploid plants. Double haploids are produced by the doubling of a set of chromosomes (1N) from a heterozygous plant to produce a completely homozygous individual. For example, see, Wan, et al., "Efficient Production of Doubled Haploid Plants Through Colchicine Treatment of Anther-Derived Maize Callus," *Theoretical and Applied Genetics*, 77:889-892 (1989) and U.S. Pat. No. 7,135,615. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, *Am. Nat.*, 93:381-382 (1959); Sharkar and Coe, *Genetics*, 54:453-464 (1966); KEMS (Deimling, Roeber, and Geiger, Vortr. Pflanzenzuchtg, 38:203-224 (1997); or KMS and ZMS (Chalyk, Bylich & Chebotar, MNL, 68:47 (1994); Chalyk & Chebotar, *Plant Breeding*, 119:363-364

(2000)); and indeterminate gametophyte (ig) mutation (Kermicle, *Science,* 166:1422-1424 (1969)). The disclosures of which are incorporated herein by reference.

Methods for obtaining haploid plants are also disclosed in Kobayashi, M., et al., *Journ. of Heredity,* 71(1):9-14 (1980); Pollacsek, M., *Agronomie* (Paris) 12(3):247-251 (1992); Cho-Un-Haing, et al., *Journ. of PlantBiol.,* 39(3):185-188 (1996); Verdoodt, L., et al., 96(2):294-300 (February 1998); Chalyk, et al., *Maize Genet Coop.,* Newsletter 68:47 (1994).

Thus, an embodiment is a process for making a substantially homozygous soybean cultivar 2564372 progeny plant by producing or obtaining a seed from the cross of soybean cultivar 2564372 and another soybean plant and applying double haploid methods to the $F_1$ seed or $F_1$ plant or to any successive filial generation. Based on studies in maize and currently being conducted in soybean, such methods would decrease the number of generations required to produce a variety with similar genetics or characteristics to soybean cultivar 2564372. See, Bernardo, R. and Kahler, A. L., *Theor. Appl. Genet.,* 102:986-992 (2001).

In particular, a process of making seed retaining the molecular marker profile of soybean variety 2564372 is contemplated, such process comprising obtaining or producing $F_1$ seed for which soybean variety 2564372 is a parent, inducing doubled haploids to create progeny without the occurrence of meiotic segregation, obtaining the molecular marker profile of soybean variety 2564372, and selecting progeny that retain the molecular marker profile of soybean cultivar 2564372.

Descriptions of other breeding methods that are commonly used for different traits and crops can be found in one of several reference books (e.g., Allard (1960); Simmonds (1979); Sneep, et al. (1979); Fehr (1987)).

Expression Vectors for Soybean Transformation: Marker Genes

Plant transformation involves the construction of an expression vector which will function in plant cells. Such a vector comprises DNA comprising a gene under control of, or operatively linked to, a regulatory element (for example, a promoter). Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well-known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley, et al., *Proc. Natl. Acad. Sci. USA,* 80:4803 (1983).

Another commonly used selectable marker gene is the hygromycin phosphotransferase gene which confers resistance to the antibiotic hygromycin. Vanden Elzen, et al., *Plant Mol. Biol.,* 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford, et al., *Plant Physiol.,* 86:1216 (1988);

Jones, et al., *Mol. Gen. Genet.,* 210:86 (1987); Svab, et al., *Plant Mol. Biol.,* 14:197 (1990); Hille, et al., *Plant Mol. Biol.,* 7:171 (1986)). Other selectable marker genes confer resistance to herbicides such as glyphosate, glufosinate, or bromoxynil (Comai, et al., *Nature,* 317:741-744 (1985); Gordon-Kamm, et al., *Plant Cell,* 2:603-618 (1990); Stalker, et al., *Science,* 242:419-423 (1988)).

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.,* 13:67 (1987); Shah, et al., *Science,* 233:478 (1986); Charest, et al., *Plant Cell Rep.,* 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., *Plant Mol. Biol. Rep.,* 5:387 (1987); Teeri, et al., *EMBO J.,* 8:343 (1989); Koncz, et al., *Proc. Natl. Acad. Sci. USA,* 84:131 (1987); DeBlock, et al., *EMBO J.,* 3:1681 (1984)).

In vivo methods for visualizing GUS activity that do not require destruction of plant tissue are available (Molecular Probes, Publication 2908, IMAGENE GREEN, pp. 1-4 (1993); Naleway, et al., *J. Cell Biol.,* 115:151a (1991)). However, these in-vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells (Chalfie, et al., *Science,* 263:802 (1994)). GFP and mutants of GFP may be used as screenable markers.

Expression Vectors for Soybean Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters: An inducible promoter is operably linked to a gene for expression in soybean. Optionally, the inducible promoter is operably linked to a nucleotide sequence encoding a signal sequence which is operably linked to a gene for expression in soybean. With an inducible promoter, the rate of transcription increases in response to an inducing agent.

Any inducible promoter can be used in an embodiment(s). See, Ward, et al., *Plant Mol. Biol.*, 22:361-366 (1993). Exemplary inducible promoters include, but are not limited to, that from the ACEI system which responds to copper (Mett, et al., *Proc. Natl. Acad. Sci. USA*, 90:4567-4571 (1993)); In2 gene from maize which responds to benzenesulfonamide herbicide safeners (Hershey, et al., *Mol. Gen Genetics*, 227:229-237 (1991); Gatz, et al., *Mol. Gen. Genetics*, 243:32-38 (1994)); or Tet repressor from Tn10 (Gatz, et al., *Mol. Gen. Genetics*, 227:229-237 (1991)). An inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena, et al., *Proc. Natl. Acad. Sci. USA*, 88:0421 (1991)).

B. Constitutive Promoters: A constitutive promoter is operably linked to a gene for expression in soybean or the constitutive promoter is operably linked to a nucleotide sequence encoding a signal sequence which is operably linked to a gene for expression in soybean.

Many different constitutive promoters can be utilized in an embodiment(s). Exemplary constitutive promoters include, but are not limited to, the promoters from plant viruses such as the 35S promoter from CaMV (Odell, et al., *Nature*, 313:810-812 (1985)) and the promoters from such genes as rice actin (McElroy, et al., *Plant Cell*, 2:163-171 (1990)); ubiquitin (Christensen, et al., *Plant Mol. Biol.*, 12:619-632 (1989); Christensen, et al., *Plant Mol. Biol.*, 18:675-689 (1992)); pEMU (Last, et al., *Theor. Appl. Genet.*, 81:581-588 (1991)); MAS (Velten, et al., *EMBO J.*, 3:2723-2730 (1984)); and maize H3 histone (Lepetit, et al., *Mol. Gen. Genetics*, 231:276-285 (1992); Atanassova, et al., *Plant Journal*, 2 (3):291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See, U.S. Pat. No. 5,659,026.

C. Tissue-Specific or Tissue-Preferred Promoters: A tissue-specific promoter is operably linked to a gene for expression in soybean. Optionally, the tissue-specific promoter is operably linked to a nucleotide sequence encoding a signal sequence which is operably linked to a gene for expression in soybean. Plants transformed with a gene of interest operably linked to a tissue-specific promoter produce the protein product of the transgene exclusively, or preferentially, in a specific tissue.

Any tissue-specific or tissue-preferred promoter can be utilized in an embodiment(s). Exemplary tissue-specific or tissue-preferred promoters include, but are not limited to, a root-preferred promoter such as that from the phaseolin gene (Murai, et al., *Science*, 23:476-482 (1983); Sengupta-Gopalan, et al., *Proc. Natl. Acad. Sci. USA*, 82:3320-3324 (1985)); a leaf-specific and light-induced promoter such as that from cab or rubisco (Simpson, et al., *EMBO J.*, 4(11): 2723-2729 (1985); Timko, et al., *Nature*, 318:579-582 (1985)); an anther-specific promoter such as that from LAT52 (Twell, et al., *Mol. Gen. Genetics*, 217:240-245 (1989)); a pollen-specific promoter such as that from Zm13 (Guerrero, et al., *Mol. Gen. Genetics*, 244:161-168 (1993)); or a microspore-preferred promoter such as that from apg (Twell, et al., *Sex. Plant Reprod.*, 6:217-224 (1993)).

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.*, 20:49 (1992); Knox, C., et al., *Plant Mol. Biol.*, 9:3-17 (1987); Lerner, et al., *Plant Physiol.*, 91:124-129 (1989); Frontes, et al., *Plant Cell*, 3:483-496 (1991); Matsuoka, et al., *Proc. Natl. Acad. Sci.*, 88:834 (1991); Gould, et al., *J. Cell. Biol.*, 108:1657 (1989); Creissen, et al., *Plant 1*, 2:129 (1991); Kalderon, et al., *Cell*, 39:499-509 (1984); Steifel, et al., *Plant Cell*, 2:785-793 (1990).

Foreign Protein Genes and Agronomic Genes: Transformation

With transgenic plants according to one embodiment, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, *Anal. Biochem.*, 114:92-6 (1981).

According to an embodiment, the transgenic plant provided for commercial production of foreign protein is a soybean plant. In another embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see, Glick and Thompson, *Methods in Plant Molecular Biology and Biotechnology*, CRC Press, Inc., Boca Raton, 269:284 (1993). Map information concerning chromosomal location is useful for proprietary protection of a subject transgenic plant.

Wang, et al. discuss "Large Scale Identification, Mapping and Genotyping of Single-Nucleotide Polymorphisms in the Human Genome," *Science*, 280:1077-1082 (1998), and similar capabilities are becoming increasingly available for the soybean genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR, and sequencing, all of which are conventional techniques. SNPs may also be used alone or in combination with other techniques.

Likewise, by means of one embodiment, plants can be genetically engineered to express various phenotypes of agronomic interest. Through the transformation of soybean, the expression of genes can be altered to enhance disease resistance, insect resistance, herbicide resistance, agronomic, grain quality, and other traits. Transformation can also be used to insert DNA sequences which control or help control male-sterility. DNA sequences native to soybean, as well as non-native DNA sequences, can be transformed into soybean and used to alter levels of native or non-native proteins. Various promoters, targeting sequences, enhancing sequences, and other DNA sequences can be inserted into the genome for the purpose of altering the expression of proteins. The interruption or suppression of the expression of a gene at the level of transcription or translation (also known as gene silencing or gene suppression) is desirable for several aspects of genetic engineering in plants.

Many techniques for gene silencing are well-known to one of skill in the art, including, but not limited to, knockouts (such as by insertion of a transposable element such as Mu (Vicki Chandler, *The Maize Handbook*, Ch. 118 (Springer-Verlag 1994)) or other genetic elements such as a FRT, Lox, or other site specific integration sites; antisense technology (see, e.g., Sheehy, et al., *PNAS USA*, 85:8805-8809 (1988) and U.S. Pat. Nos. 5,107,065, 5,453,566, and 5,759,829); co-suppression (e.g., Taylor, *Plant Cell*, 9:1245 (1997); Jorgensen, *Trends Biotech.*, 8(12):340-344 (1990); Flavell, *PNAS USA*, 91:3490-3496 (1994); Finnegan, et al., *Bio/Technology*, 12:883-888 (1994); Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); Montgomery, et al., *PNAS USA*, 95:15502-15507 (1998)), virus-induced gene silencing (Burton, et al., *Plant Cell*, 12:691-705 (2000); Baulcombe, *Curr. Op. Plant Bio.*, 2:109-113 (1999)); target-RNA-specific ribozymes (Haseloff, et al., *Nature*, 334:585-591 (1988)); hairpin structures (Smith, et al., *Nature*, 407:319-320 (2000); U.S. Pat. Nos. 6,423,885, 7,138,565, 6,753,139, and 7,713,715); MicroRNA (Aukerman & Sakai, *Plant Cell*, 15:2730-2741 (2003)); ribozymes (Steinecke, et al., *EMBO J.*, 11:1525 (1992); Perriman, et al., *Antisense Res. Dev.*, 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); and other methods or combinations of the above methods known to those of skill in the art.

Methods for Soybean Transformation

Numerous methods for plant transformation have been developed including biological and physical plant transformation protocols. See, for example, Miki, et al., "Procedures for Introducing Foreign DNA into Plants," in Methods in Plant Molecular Biology and Biotechnology, Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber, et al., "Vectors for Plant Transformation," in Methods in Plant Molecular Biology and Biotechnology, Glick and Thompson Eds., CRC Press, Inc., Boca Raton, pp. 89-119 (1993).

A. *Agrobacterium*-mediated Transformation: One method for introducing an expression vector into plants is based on the natural transformation system of *Agrobacterium*. See, for example, Horsch, et al., *Science*, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Reports*, 8:238 (1989). See also, U.S. Pat. No. 5,563,055 (Townsend and Thomas), issued Oct. 8, 1996.

B. Direct Gene Transfer: Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford, et al., *Part. Sci. Technol.*, 5:27 (1987); Sanford, J. C., *Trends Biotech.*, 6:299 (1988); Klein, et al., *Bio/Tech.*, 6:559-563 (1988); Sanford, J. C., *Physiol Plant*, 7:206 (1990); Klein, et al., *Biotechnology*, 10:268 (1992). See also, U.S. Pat. No. 5,015,580 (Christou, et al.), issued May 14, 1991 and U.S. Pat. No. 5,322,783.

Another method for physical delivery of DNA to plants is sonication of target cells. Zhang, et al., *Bio/Technology*, 9:996 (1991). Alternatively, liposome and spheroplast fusion have been used to introduce expression vectors into plants. Deshayes, et al., *EMBO J.*, 4:2731 (1985); Christou, et al., *Proc Natl. Acad. Sci. USA*, 84:3962 (1987). Direct uptake of DNA into protoplasts using $CaCl_2$) precipitation, polyvinyl alcohol or poly-L-ornithine have also been reported. Hain, et al., *Mol. Gen. Genet.*, 199:161 (1985) and Draper, et al., *Plant Cell Physiol.*, 23:451 (1982). Electroporation of protoplasts and whole cells and tissues has also been described (D'Halluin, et al., *Plant Cell*, 4:1495-1505 (1992); and Spencer, et al., *Plant Mol. Biol.*, 24:51-61 (1994)).

Following transformation of soybean target tissues, expression of the above-described selectable marker genes allows for preferential selection of transformed cells, tissues, and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular soybean line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Likewise, by means of one embodiment, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example, Jones, et al., *Science*, 266:789 (1994) (cloning of the tomato Cf-9 gene for resistance to *Cladosporium fulvum*); Martin, et al., *Science*, 262:1432 (1993) (tomato Pto gene for resistance to *Pseudomonas syringae* pv. tomato encodes a protein kinase); Mindrinos, et al., *Cell*, 78:1089 (1994) (*Arabidopsis* RSP2 gene for resistance to *Pseudomonas syringae*); McDowell & Woffenden, *Trends Biotechnol.*, 21(4):178-83 (2003); and Toyoda, et al., *Transgenic Res.*, 11 (6):567-82 (2002).

B. A gene conferring resistance to a pest, such as soybean cyst nematode. See, e.g., U.S. Pat. No. 5,994,627.

C. A *Bacillus thuringiensis* protein, a derivative thereof or a synthetic polypeptide modeled thereon. See, for example, Geiser, et al., *Gene*, 48:109 (1986), who disclose the cloning and nucleotide sequence of a Bt δ-endotoxin gene. Moreover, DNA molecules encoding 6-endotoxin genes can be purchased from American Type Culture Collection, Manassas, Va., for example, under ATCC Accession Nos. 40098, 67136, 31995, and 31998.

D. A lectin. See, for example, Van Damme, et al., *Plant Molec. Biol.*, 24:25 (1994), who disclose the nucleotide sequences of several *Clivia miniata* mannose-binding lectin genes.

E. A vitamin-binding protein such as avidin. See, International Application No. PCT/US1993/006487, which teaches the use of avidin and avidin homologues as larvicides against insect pests.

F. An enzyme inhibitor, for example, a protease or proteinase inhibitor or an amylase inhibitor. See, for example, Abe, et al., *J. Biol. Chem.*, 262:16793 (1987) (nucleotide sequence of rice cysteine proteinase inhibitor); Huub, et al., *Plant Molec. Biol.*, 21:985 (1993) (nucleotide sequence of cDNA encoding tobacco proteinase inhibitor I); Sumitani, et al., *Biosci. Biotech. Biochem.*, 57:1243 (1993) (nucleotide sequence of *Streptomyces nitrosporeus* α-amylase inhibitor); and U.S. Pat. No. 5,494,813.

G. An insect-specific hormone or pheromone, such as an ecdysteroid or juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor); Pratt, et al., *Biochem. Biophys. Res. Comm.*, 163:1243 (1989) (an allostatin is identified in *Diploptera puntata*); Chattopadhyay, et al., *Critical Reviews in Microbiology*, 30(1):33-54 (2004); Zjawiony, *J. Nat. Prod.*, 67(2):300-310 (2004); Carlini & Grossi-de-Sa, *Toxicon*, 40(11):1515-1539 (2002); Ussuf, et al., *Curr Sci.*, 80(7):847-853 (2001); Vasconcelos & Oliveira, *Toxicon*, 44(4):385-403 (2004). See also, U.S. Pat. No. 5,266,317 which discloses genes encoding insect-specific, paralytic neurotoxins.

I. An insect-specific venom produced in nature by a snake, a wasp, etc. For example, see, Pang, et al., *Gene*, 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative, or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, U.S. Pat. No. 5,955,653 which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Molec. Biol.*, 23:691 (1993), who teach the nucleotide sequence of a cDNA encoding tobacco hornworm chitinase, and Kawalleck, et al., *Plant Molec. Biol.*, 21:673 (1993), who provide the nucleotide sequence of the parsley ubi4-2 polyubiquitin gene, U.S. Pat. Nos. 7,145,060, 7,087,810, and 6,563,020.

L. A molecule that stimulates signal transduction. For example, see the disclosure by Botella, et al., *Plant Molec. Biol.*, 24:757 (1994), of nucleotide sequences for mung bean calmodulin cDNA clones, and Griess, et al., *Plant Physiol.*, 104:1467 (1994), who provide the nucleotide sequence of a maize calmodulin cDNA clone.

M. A hydrophobic moment peptide. See, U.S. Pat. No. 5,580,852, which discloses peptide derivatives of tachyplesin which inhibit fungal plant pathogens, and U.S. Pat. No. 5,607,914 which teaches synthetic antimicrobial peptides that confer disease resistance.

N. A membrane permease, a channel former or a channel blocker. For example, see the disclosure of Jaynes, et al., *Plant Sci*, 89:43 (1993), of heterologous expression of a cecropin-13 lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., *Ann. Rev. Phytopathol.*, 28:451 (1990). Coat protein-mediated resistance has been conferred upon transformed plants against alfalfa mosaic virus, cucumber mosaic virus, and tobacco mosaic virus.

P. An insect-specific antibody or an immunotoxin derived therefrom. Thus, an antibody targeted to a critical metabolic function in the insect gut would inactivate an affected enzyme, killing the insect.

Q. A virus-specific antibody. See, for example, Tavladoraki, et al., *Nature*, 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See, Lamb, et al., *Bio/Technology*, 10:1436 (1992). The cloning and characterization of a gene which encodes a bean endopolygalacturonase-inhibiting protein is described by Toubart, et al., *Plant J.*, 2:367 (1992).

S. A developmental-arrestive protein produced in nature by a plant. For example, Logemann, et al., *Bio/Technology*, 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology*, 5(2) (1995); Pieterse & Van Loon, *Curr. Opin. Plant Bio.*, 7(4):456-64 (2004); and Somssich, *Cell*, 113(7):815-6 (2003).

U. Antifungal genes. See, Cornelissen and Melchers, *Plant Physiol.*, 101:709-712 (1993); Parijs, et al., *Planta*, 183:258-264 (1991); and Bushnell, et al., *Can. J of Plant Path.*, 20(2):137-149 (1998). See also, U.S. Pat. No. 6,875,907.

V. Detoxification genes, such as for fumonisin, beauvericin, moniliformin, and zearalenone and their structurally-related derivatives. See, U.S. Pat. No. 5,792,931.

W. Cystatin and cysteine proteinase inhibitors. See, U.S. Pat. No. 7,205,453.

X. Defensin genes. See, U.S. Pat. Nos. 6,911,577, 7,855,327, 7,855,328, 7,897,847, 7,910,806, 7,919,686, and 8,026,415.

Y. Genes conferring resistance to nematodes, and in particular soybean cyst nematodes. See, U.S. Pat. Nos. 5,994,627 and 6,294,712; Urwin, et al., *Planta*, 204:472-479 (1998); Williamson, *Curr Opin Plant Bio.*, 2(4):327-31 (1999).

Z. Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7, and other Rps genes. See, for example, Shoemaker, et al., *Phytophthora* Root Rot Resistance Gene Mapping in Soybean, Plant Genome IV Conference, San Diego, Calif. (1995).

AA. Genes that confer resistance to Brown Stem Rot, such as described in U.S. Pat. No. 5,689,035 and incorporated by reference for this purpose.

Any of the above-listed disease or pest resistance genes (A-AA) can be introduced into the claimed soybean cultivar through a variety of means including, but not limited to, transformation and crossing.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee, et al., *EMBO J.*, 7:1241 (1988) and Mild, et al., *Theor. Appl. Genet.*, 80:449 (1990), respectively.

B. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT) and *Streptomyces hygroscopicus* PAT bar genes), pyridinoxy or phenoxy proprionic acids, and cyclohexanediones (ACCase inhibitor-encoding genes). See, for example, U.S. Pat. No. 4,940,835 which discloses the nucleotide sequence of a form of EPSPS which can confer glyphosate resistance. U.S. Pat. No. 5,627,061 which describes genes encoding EPSPS enzymes. See also, U.S. Pat. Nos. 6,566,587, 6,338,961, 6,248,876, 6,040,497, 5,804,425, 5,633,435, 5,145,783, 4,971,908, 5,312,910, 5,188,642, 4,940,835, 5,866,775, 6,225,114, 6,130,366, 5,310,667, 4,535,060, 4,769,061, 5,633,448, 5,510,471, 6,803,501, RE 36,449, RE 37,287, and 5,491,288, which are incorporated herein by reference for this purpose. Glyphosate resistance is also imparted to plants that express a gene that encodes a glyphosate oxido-reductase enzyme, as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. Pat. No. 7,462,481. A DNA molecule encoding a mutant aroA gene can be obtained under ATCC Accession No. 39256, and the nucleotide sequence of the mutant gene is disclosed in U.S. Pat. No. 4,769,061. European Patent Appl. No. 0333033 and U.S. Pat. No. 4,975,374 disclose nucleotide sequences of glutamine synthetase genes which confer resistance to herbicides such as L-phosphinothricin. The nucleotide sequence of a PAT gene is provided in European Patent No. 0242246 to Leemans, et al. DeGreef, et al., *Bio/Technology*, 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall, et al., *Theor. Appl. Genet.*, 83:435 (1992).

C. An herbicide that inhibits photosynthesis, such as a triazine (psbA and gs+ genes) and a benzonitrile (nitrilase gene). Przibila, et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes, et al., *Biochem. J.*, 285:173 (1992). Protoporphyrinogen oxidase (PPO) is the target of the PPO-inhibitor class of herbicides; a PPO-inhibitor resistant PPO gene was recently identified in *Amaranthus tuberculatus* (Patzoldt et al., *PNAS*, 103(33):12329-2334, 2006). The herbicide methyl viologen inhibits $CO_2$ assimilation. Foyer et al. (*Plant Physiol.*, 109:1047-1057, 1995) describe a plant overexpressing glutathione reductase (GR) which is resistant to methyl viologen treatment. Bromoxynil resistance by introducing a chimeric gene containing the bxn gene (*Science*, 242(4877): 419-23, 1988).

D. Acetohydroxy acid synthase, which has been found to make plants that express this enzyme resistant to multiple types of herbicides, has been introduced into a variety of plants. See, Hattori, et al., *Mol. Gen. Genet.*, 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.*, 106:17 (1994)); genes for glutathione reductase and superoxide dismutase (Aono, et al., *Plant Cell Physiol.*, 36:1687 (1995)); and genes for various phosphotransferases (Datta, et al., *Plant Mol. Biol.*, 20:619 (1992)).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and 6,084,155.

Any of the above listed herbicide genes (A-E) can be introduced into the claimed soybean cultivar through a variety of means including but not limited to transformation and crossing.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See, Knultzon, et al., *Proc. Natl. Acad. Sci. USA,* 89:2625 (1992).

B. Decreased phytate content: 1) Introduction of a phytase-encoding gene enhances breakdown of phytate, adding more free phosphate to the transformed plant. For example, see, Van Hartingsveldt, et al., *Gene,* 127:87 (1993), for a disclosure of the nucleotide sequence of an *Aspergillus niger* phytase gene. 2) Up-regulation of a gene that reduces phytate content. In maize, this, for example, could be accomplished by cloning and then re-introducing DNA associated with one or more of the alleles, such as the LPA alleles, identified in maize mutants characterized by low levels of phytic acid, such as in Raboy, et al., *Maydica,* 35:383 (1990), and/or by altering inositol kinase activity as in, for example, U.S. Pat. Nos. 7,425,442, 7,714,187, 6,197, 561, 6,2191,224, 6,855,869, 6,391,348, 6,197,561, and 6,291,224; U.S. Publ. Nos. 2003/000901, 2003/0009011, and 2006/272046; and International Pub. Nos. WO 98/45448, and WO 01/04147.

C. Modified carbohydrate composition effected, for example, by transforming plants with a gene coding for an enzyme that alters the branching pattern of starch, or a gene altering thioredoxin, such as NTR and/or TRX (See, U.S. Pat. No. 6,531,648, which is incorporated by reference for this purpose), and/or a gamma zein knock out or mutant, such as cs27 or TUSC27 or en27 (See, U.S. Pat. Nos. 6,858,778, 7,741,533 and U.S. Publ. No. 2005/0160488, which are incorporated by reference for this purpose). See, Shiroza, et al., *J. Bacteriol.,* 170:810 (1988) (nucleotide sequence of *Streptococcus mutans* fructosyltransferase gene); Steinmetz, et al., *Mol. Gen. Genet.,* 200:220 (1985) (nucleotide sequence of *Bacillus subtilis* levansucrase gene); Pen, et al., *Bio/Technology,* 10:292 (1992) (production of transgenic plants that express *Bacillus licheniformis* α-amylase); Elliot, et al., *Plant Molec. Biol.,* 21:515 (1993) (nucleotide sequences of tomato invertase genes); Søgaard, et al., *J. Biol. Chem.,* 268:22480-22484 (1993) (site-directed mutagenesis of barley α-amylase gene); Fisher, et al., *Plant Physiol.,* 102:1045 (1993) (maize endosperm starch branching enzyme II); International Pub. No. WO 99/10498 (improved digestibility and/or starch extraction through modification of UDP-D-xylose 4-epimerase, Fragile 1 and 2, Ref 1, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

D. Elevated oleic acid via FAD-2 gene modification and/or decreased linolenic acid via FAD-3 gene modification. See, U.S. Pat. Nos. 5,952,544, 6,063,947, and 6,323, 392. Linolenic acid is one of the five most abundant fatty acids in soybean seeds. The low oxidative stability of linolenic acid is one reason that soybean oil undergoes partial hydrogenation. When partially hydrogenated, all unsaturated fatty acids form trans fats. Soybeans are the largest source of edible-oils in the U.S. and 40% of soybean oil production is partially hydrogenated. The consumption of trans fats increases the risk of heart disease. Regulations banning trans fats have encouraged the development of low linolenic soybeans. Soybeans containing low linolenic acid percentages create a more stable oil requiring hydrogenation less often. This provides trans fat free alternatives in products such as cooking oil.

E. Altering conjugated linolenic or linoleic acid content, such as in U.S. Pat. No. 6,593,514. Altering LEC1, AGP, Dek1, Superal1, milps, and various lpa genes, such as Ipa1, Ipa3, hpt, or hggt. See, for example, U.S. Pat. Nos. 7,122, 658, 7,342,418, 6,232,529, 7,888,560, 6,423,886, 6,197,561, 6,825,397 and 7,157,621; U.S. Publ. No. 2003/0079247; International Publ. No. WO 2003/011015; and Rivera-Madrid, R., et al., *Proc. Natl. Acad. Sci.,* 92:5620-5624 (1995).

F. Altered antioxidant content or composition, such as alteration of tocopherol or tocotrienols. See, for example, U.S. Pat. Nos. 6,787,683, 7,154,029 and International Publ. No. WO 00/68393 (involving the manipulation of antioxidant levels through alteration of a phytl prenyl transferase (ppt)); and U.S. Pat. Nos. 7,154,029 and 7,622,658 (through alteration of a homogentisate geranyl geranyl transferase (hggt)).

G. Altered essential seed amino acids. See, for example, U.S. Pat. No. 6,127,600 (method of increasing accumulation of essential amino acids in seeds); U.S. Pat. No. 6,080,913 (binary methods of increasing accumulation of essential amino acids in seeds); U.S. Pat. No. 5,990,389 and International Publ. No. WO 95/15392 (high lysine); U.S. Pat. No. 5,850,016 (alteration of amino acid compositions in seeds); U.S. Pat. No. 5,885,802 (high methionine); U.S. Pat. No. 5,885,801 and International Publ. No. WO96/01905 (high threonine); U.S. Pat. Nos. 6,664,445, 7,022,895, 7,368,633, and 7,439,420 (plant amino acid biosynthetic enzymes); U.S. Pat. Nos. 6,459,019 and 9,381,485 (increased lysine and threonine); U.S. Pat. No. 6,441,274 (plant tryptophan synthase beta subunit); U.S. Pat. No. 6,346,403 (methionine metabolic enzymes); U.S. Pat. No. 5,939,599 (high sulfur); U.S. Pat. No. 5,912,414 (increased methionine); U.S. Pat. No. 5,633,436 (increasing sulfur amino acid content); U.S. Pat. No. 5,559,223 (synthetic storage proteins with defined structure containing programmable levels of essential amino acids for improvement of the nutritional value of plants); U.S. Pat. No. 6,194,638 (hemicellulose); U.S. Pat. No. 7,098,381 (UDPGdH); U.S. Pat. No. 6,194,638 (RGP); U.S. Pat. Nos. 6,399,859, 6,930,225, 7,179,955, 6,803,498, 5,850,016, and 7,053,282 (alteration of amino acid compositions in seeds); WO 99/29882 (methods for altering amino acid content of proteins); U.S. application Ser. No. 09/297, 418 (proteins with enhanced levels of essential amino acids); WO 98/45458 (engineered seed protein having higher percentage of essential amino acids); WO 01/79516; and U.S. Pat. Nos. 6,803,498, 6,930,225, 7,307,149, 7,524,933, 7,579,443, 7,838,632, 7,851,597, and 7,982,009 (maize cellulose synthases).

4. Genes that Control Male Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

A. Introduction of a deacetylase gene under the control of a tapetum-specific promoter and with the application of the chemical N-Ac-PPT. See, U.S. Pat. No. 6,384,304.

B. Introduction of various stamen-specific promoters. See, U.S. Pat. Nos. 5,639,948 and 5,589,610.

C. Introduction of the barnase and the barstar genes. See, Paul, et al., *Plant Mol. Biol.,* 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640, all of which are hereby incorporated by reference.

5. Genes that Create a Site for Site Specific DNA Integration:

This includes the introduction of FRT sites that may be used in the FLP/FRT system and/or Lox sites that may be used in the Cre/Loxp system. See, for example, Lyznik, et al., Site-Specific Recombination for Genetic Engineering in Plants, *Plant Cell Rep,* 21:925-932 (2003) and U.S. Pat. No. 6,187,994, which are hereby incorporated by reference. Other systems that may be used include the Gin recombinase of phage Mu (Maeser, et al. (1991); Vicki Chandler, The Maize Handbook, Ch. 118 (Springer-Verlag 1994)); the Pin recombinase of *E. coli* (Enomoto, et al. (1983)); and the R/RS system of the pSRi plasmid (Araki, et al. (1992)).

6. Genes that Affect Abiotic Stress Resistance:

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see U.S. Pat. No. 6,653,535 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, 6,946,586, 7,238,860, 7,635,800, 7,135,616, 7,193,129, and 7,601,893; and International Publ. Nos. WO 2001/026459, WO 2001/035725, WO 2001/035727, WO 2001/036444, WO 2001/036597, WO 2001/036598, WO 2002/015675, and WO 2002/077185, describing genes, including CBF genes and transcription factors effective in mitigating the negative effects of freezing, high salinity, and drought on plants, as well as conferring other positive effects on plant phenotype; U.S. Publ. No. 2004/0148654, where abscisic acid is altered in plants resulting in improved plant phenotype, such as increased yield and/or increased tolerance to abiotic stress; U.S. Pat. Nos. 6,992,237, 6,429,003, 7,049,115, and 7,262,038, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and U.S. application Ser. No. 09/856,834. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See for example, U.S. Pat. Nos. 6,140,085, and 6,265,637 (CO); U.S. Pat. No. 6,670,526 (ESD4); U.S. Pat. No. 6,573,430 and 7,157,279 (TFL); U.S. Pat. No. 6,713,663 (FT); U.S. Pat. Nos. 6,794,560, 6,307,126 (GAI); U.S. Pat. No. 7,045,682 (VRN1); U.S. Pat. Nos. 6,949,694 and 7,253,274 (VRN2); U.S. Pat. No. 6,887,708 (GI); U.S. Pat. No. 7,320,158 (FRI); U.S. Pat. No. 6,307,126 (GAI); U.S. Pat. Nos. 6,762,348 and 7,268,272 (D8 and Rht); and U.S. Pat. Nos. 7,345,217, 7,511,190, 7,659,446, and 7,825,296 (transcription factors).

Genetic Marker Profile Through SSR and First Generation Progeny

In addition to phenotypic observations, a plant can also be identified by its genotype. The genotype of a plant can be characterized through a genetic marker profile which can identify plants of the same variety, or a related variety, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs). For example, see, Cregan, et al., "An Integrated Genetic Linkage Map of the Soybean Genome," *Crop Science,* 39:1464-1490 (1999) and Berry, et al., "Assessing Probability of Ancestry Using Simple Sequence Repeat Profiles: Applications to Maize Inbred Lines and Soybean Varieties," *Genetics,* 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for soybean cultivar 2564372.

Primers and PCR protocols for assaying these and other markers are disclosed in the Soybase (sponsored by the USDA Agricultural Research Service and Iowa State University). In addition to being used for identification of soybean variety 2564372, and plant parts and plant cells of soybean variety 2564372, the genetic profile may be used to identify a soybean plant produced through the use of soybean cultivar 2564372 or to verify a pedigree for progeny plants produced through the use of soybean cultivar 2564372. The genetic marker profile is also useful in breeding and developing backcross conversions.

One embodiment comprises a soybean plant characterized by molecular and physiological data obtained from the sample of said variety deposited with a Budapest Depository. Further provided by the embodiment(s) is a soybean plant formed by the combination of the disclosed soybean plant or plant cell with another soybean plant or cell and comprising the homozygous alleles of the variety. "Cell" as used herein includes a plant cell, whether isolated, in tissue culture or incorporated in a plant or plant part.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present ("linkage" refers to a phenomenon wherein alleles on the same chromosome tend to segregate together more often than expected by chance if their transmission was independent). Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties, it is preferable if all SSR profiles are performed in the same lab.

Primers used are publicly available and may be found in the Soybase or Cregan supra. See also, U.S. application Ser. No. 09/581,970 (Nucleotide Polymorphisms in Soybean); U.S. Pat. No. 6,162,967 (Positional Cloning of Soybean Cyst Nematode Resistance Genes); and U.S. Pat. No. 7,288,386 (Soybean Sudden Death Syndrome Resistant Soybeans and Methods of Breeding and Identifying Resistant Plants), the disclosure of which are incorporated herein by reference.

The SSR profile of soybean plant 2564372 can be used to identify plants comprising soybean cultivar 2564372 as a parent, since such plants will comprise the same homozygous alleles as soybean cultivar 2564372. Because the soybean variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of soybean cultivar 2564372 in their development, such as soybean cultivar 2564372 comprising a backcross conversion, transgene, or genetic sterility factor, may be identified by having a molecular marker profile with a high percent identity to soybean cultivar 2564372. Such a percent identity might be 95%, 96%, 97%, 98%, 99%, 99.5%, or 99.9% identical to soybean cultivar 2564372. Percent identity refers to the comparison of the homozygous alleles of two soybean varieties. Percent identity or percent similarity is determined by comparing a statistically significant number of the homozygous alleles of two developed varieties. For example, a percent identity of 90% between soybean variety 1 and soybean variety 2 means that the two varieties have the same allele at 90% of their loci.

The SSR profile of soybean cultivar 2564372 can also be used to identify essentially derived varieties and other progeny varieties developed from the use of soybean cultivar 2564372, as well as cells and other plant parts thereof. Such plants may be developed using the markers, for example, identified in U.S. Pat. Nos. 6,162,967, and 7,288,386. Progeny plants and plant parts produced using soybean cultivar 2564372 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from soybean variety, as measured by either percent identity or percent similarity. Such progeny may be further characterized as being within a pedigree distance of soybean cultivar 2564372, such as within 1, 2, 3, 4, or 5 or less cross-pollinations to a soybean plant other than soybean cultivar 2564372 or a plant that has soybean cultivar 2564372 as a progenitor. Unique molecular profiles may be identified with other molecular tools such as SNPs and RFLPs.

While determining the SSR genetic marker profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an $F_1$ progeny produced from such variety, and progeny produced from such variety.

Tissue Culture

Further reproduction of the variety can occur by tissue culture and regeneration. Tissue culture of various tissues of soybeans and regeneration of plants therefrom is well-known and widely published. For example, reference may be had to Komatsuda, T., et al., *Crop Sci.*, 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al., *Plant Cell Reports*, 11:285-289 (1992); Pandey, P., et al., *Japan J. Breed.*, 42:1-5 (1992); and Shetty, K., et al., *Plant Science*, 81:245-251 (1992); as well as U.S. Pat. Nos. 5,024,944 and 5,008,200. Thus, another aspect or embodiment is to provide cells which upon growth and differentiation produce soybean plants having the physiological and morphological characteristics of soybean cultivar 2564372.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Plant Products

The seed of soybean cultivar 2564372, the plant produced from the seed, the hybrid soybean plant produced from the crossing of the variety with any other soybean plant, hybrid seed, and various parts of the hybrid soybean plant can be utilized for plant products. Industrial uses include but are not limiting to, human food, livestock feed, and as a raw material in industry.

As used herein the term plant product will be understood to mean the product derived from or produced by a plant of soybean cultivar 2564372, for example, the tissues or structures of the plant of soybean cultivar 2564372 such as the flower, fruit, seed, grain, leaves, stems etc., produced by the plant. Further, the soybean seeds produced from or derived from soybean cultivar 2564372 can be crushed, or a component of the soybean seeds can be extracted, in order to comprise a plant product, such as protein concentrate, protein isolate, soybean hulls, meal, flour, or oil for a food or feed product.

The soybean is the world's leading source of vegetable oil and protein meal. The oil extracted from soybeans is used for cooking oil, margarine, and salad dressings. Soybean oil is composed of saturated, monounsaturated, and polyunsaturated fatty acids. It has a typical composition of 11% palmitic, 4% stearic, 25% oleic, 50% linoleic, and 9% linolenic fatty acid content ("Economic Implications of Modified Soybean Traits Summary Report," Iowa Soybean Promotion Board and American Soybean Association Special Report 92S (May 1990)). Changes in fatty acid composition for improved oxidative stability and nutrition are constantly sought after. Industrial uses of soybean oil, which is subjected to further processing, include ingredients for paints, plastics, fibers, detergents, cosmetics, lubricants, and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils to produce the desired type of oil or fat.

Soybean cultivar 2564372 can be used to produce soybean oil. To produce soybean oil, the soybeans harvested from soybean cultivar 2564372 are cracked, adjusted for moisture content, rolled into flakes and the oil is solvent-extracted from the flakes with commercial hexane. The oil is then refined, blended for different applications, and sometimes hydrogenated. Soybean oils, both liquid and partially hydrogenated, are used domestically and exported, sold as "vegetable oil" or are used in a wide variety of processed foods.

Soybeans are also used as a food source for both animals and humans. Soybeans are widely used as a source of protein for poultry, swine, and cattle feed. During processing of whole soybeans, the fibrous hull is removed and the oil is extracted. The remaining soybean meal is a combination of carbohydrates and approximately 50% protein.

Soybean cultivar 2564372 can be used to produce meal. After oil is extracted from whole soybeans harvested from soybean cultivar 2564372, the remaining material or "meal" is "toasted" (a misnomer because the heat treatment is with moist steam) and ground in a hammer mill. Soybean meal is an essential element of the American production method of growing farm animals, such as poultry and swine, on an industrial scale that began in the 1930s; and more recently the aquaculture of catfish. Ninety-eight percent of the U.S. soybean crop is used for livestock feed. Soybean meal is also used in lower end dog foods. Soybean meal produced from soybean cultivar 2564372 can also be used to produce soybean protein concentrate and soybean protein isolate.

In addition to soybean meal, soybean cultivar 2564372 can be used to produce soy flour. Soy flour refers to defatted soybeans where special care was taken during desolventizing (not toasted) to minimize denaturation of the protein and to retain a high Nitrogen Solubility Index (NSI) in making the flour. Soy flour is the starting material for production of soy concentrate and soy protein isolate. Defatted soy flour is obtained from solvent extracted flakes, and contains less than 1% oil. Full-fat soy flour is made from unextracted, dehulled beans, and contains about 18% to 20% oil. Due to its high oil content, a specialized Alpine Fine Impact Mill must be used for grinding rather than the more common hammer mill. Low-fat soy flour is made by adding back some oil to defatted soy flour. The lipid content varies according to specifications, usually between 4.5% and 9%. High-fat soy flour can also be produced by adding back soybean oil to defatted flour at the level of 15%. Lecithinated soy flour is made by adding soybean lecithin to defatted, low-fat or high-fat soy flours to increase their dispersibility and impart emulsifying properties. The lecithin content varies up to 15%.

For human consumption, soybean cultivar 2564372 can be used to produce edible protein ingredients which offer a healthier, less expensive replacement for animal protein in meats, as well as in dairy-type products. The soybeans produced by soybean cultivar 2564372 can be processed to produce a texture and appearance similar to many other foods. For example, soybeans are the primary ingredient in many dairy product substitutes (e.g., soy milk, margarine, soy ice cream, soy yogurt, soy cheese, and soy cream cheese) and meat substitutes (e.g., veggie burgers). These substitutes are readily available in most supermarkets. Although soy milk does not naturally contain significant amounts of digestible calcium (the high calcium content of soybeans is bound to the insoluble constituents and remains in the soy pulp), many manufacturers of soy milk sell calcium-enriched products as well. Soy is also used in tempe, where the beans (sometimes mixed with grain) are fermented into a solid cake.

Additionally, soybean cultivar 2564372 can be used to produce various types of "fillers" in meat and poultry products. Food service, retail, and institutional (primarily school lunch and correctional) facilities regularly use such "extended" products, that is, products which contain soy fillers. Extension may result in diminished flavor, but fat and cholesterol are reduced by adding soy fillers to certain products. Vitamin and mineral fortification can be used to make soy products nutritionally equivalent to animal protein; the protein quality is already roughly equivalent.

Agricultural Treatment Agents

A plant, or its environment, can be contacted with a wide variety of "agriculture treatment agents." As used herein, an "agriculture treatment agent", or "treatment agent", or "agent" can refer to any exogenously provided compound that can be brought into contact with a plant tissue (e.g. a seed) or its environment that affects a plant's growth, development and/or performance, including agents that affect other organisms in the plant's environment when those effects subsequently alter a plant's performance, growth, and/or development (e.g. an insecticide that kills plant pathogens in the plant's environment, thereby improving the ability of the plant to tolerate the insect's presence). Agriculture treatment agents also include a broad range of chemicals and/or biological substances that are applied to seeds, in which case they are commonly referred to as seed treatments and/or seed dressings. Seed treatments are commonly applied as either a dry formulation or a wet slurry or liquid formulation prior to planting and, as used herein, generally include any agriculture treatment agent including growth regulators, micronutrients, nitrogen-fixing microbes, and/or inoculants. Agriculture treatment agents include pesticides (e.g. fungicides, insecticides, bactericides, etc.) hormones (abscisic acids, auxins, cytokinins, gibberellins, etc.) herbicides (e.g. glyphosate, atrazine, 2,4-D, dicamba, etc.), nutrients (e.g. a plant fertilizer), and/or a broad range of biological agents, for example a seed treatment inoculant comprising a microbe that improves crop performance, e.g. by promoting germination and/or root development. In certain embodiments, the agriculture treatment agent acts extracellularly within the plant tissue, such as interacting with receptors on the outer cell surface. In some embodiments, the agriculture treatment agent enters cells within the plant tissue.

In certain embodiments, the agriculture treatment agent remains on the surface of the plant and/or the soil near the plant. In certain embodiments, the agriculture treatment agent is contained within a liquid. Such liquids include, but are not limited to, solutions, suspensions, emulsions, and colloidal dispersions. In some embodiments, liquids described herein will be of an aqueous nature. However, in various embodiments, such aqueous liquids that comprise water can also comprise water insoluble components, can comprise an insoluble component that is made soluble in water by addition of a surfactant, or can comprise any combination of soluble components and surfactants. In certain embodiments, the application of the agriculture treatment agent is controlled by encapsulating the agent within a coating, or capsule (e.g. microencapsulation). In certain embodiments, the agriculture treatment agent comprises a nanoparticle and/or the application of the agriculture treatment agent comprises the use of nanotechnology.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One embodiment may be embodied in other specific forms without departing from its spirit or essential characteristics. The described embodiments are to be considered in all respects only as illustrative and not restrictive. All changes which come within the meaning and range of equivalency of the claims are to be embraced within their scope.

Various embodiments, include components, methods, processes, systems and/or apparatus substantially as depicted and described herein, including various embodiments, sub-combinations, and subsets thereof. Those of skill in the art will understand how to make and use an embodiment(s) after understanding the present disclosure.

The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the embodiment(s) requires more features than are expressly recited in each claim. Rather, as the following claims reflect, inventive aspects lie in less than all features of a single foregoing disclosed embodiment. Thus, the following claims are hereby incorporated into this Detailed Description.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed.

DEPOSIT INFORMATION

A deposit of the Benson Hill Seeds, Inc. proprietary soybean cultivar 2564372 disclosed above and recited in the appended claims has been made and accepted under the Budapest Treaty with the Provasoli-Guillard National Center for Marine Algae and Microbiota, Bigelow Laboratory for Ocean Sciences (NCMA), 60 Bigelow Drive, East Boothbay, Me. 04544. The date of deposit was Apr. 28, 2021. The NCMA No. is 202104024. The deposit of at least 625 seeds was taken from the same deposit maintained by Benson Hill Seeds, Inc. since prior to the filing date of this application. The deposit will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

What is claimed is:

1. A plant or a seed of soybean cultivar 2564372, wherein a representative sample of seed of said cultivar is deposited under NCMA No. 202104024.

2. A soybean plant, or a part thereof, of the plant or seed of claim 1, wherein the plant or plant part comprises at least one cell of soybean cultivar 2564372.

3. A tissue culture comprising at least one cell or protoplast of the plant or plant part of claim 2.

4. A method for producing a soybean seed, wherein the method comprises fertilizing a soybean plant and harvesting the resultant soybean seed, wherein the soybean plant is the soybean plant of claim 1.

5. A soybean seed produced by the method of claim 4, wherein the resulting soybean seed is an $F_1$ offspring or the product of self-fertilization.

6. A soybean plant, or a part thereof, produced by growing the seed of claim 5.

7. A method of producing a plant derived from soybean cultivar 2564372 comprising an added desired trait, wherein the method comprises introducing at least one mutation in a nucleic acid sequence of the soybean plant, or plant part thereof, or seed of claim 1, wherein the mutation confers the desired trait to at least one cell of soybean cultivar 2564372.

8. A method of producing a plant derived from soybean cultivar 2564372, wherein a representative sample of seed of said cultivar is deposited under NCMA No. 202104024, comprising an added desired trait, wherein the method comprises introducing at least one nucleic acid sequence conferring the desired trait to said plant by backcrossing or transformation.

9. A soybean plant produced by the method of claim 8, wherein the plant comprises the desired trait and the physiological and morphological characteristics of soybean cultivar 2564372.

10. The soybean plant of claim 9, wherein the desired trait is selected from the group comprising male sterility, herbicide tolerance, pest tolerance, disease tolerance, modified fatty acid metabolism, modified carbohydrate metabolism, modified seed yield, modified seed oil, modified seed protein, modified lodging resistance, modified shattering, modified iron-deficiency chlorosis, modified water use efficiency, and/or combinations thereof and the physiological and morphological characteristics of soybean cultivar 2564372.

11. A method of producing a plant product comprising collecting a plant product from the plant of claim 1, or plant part thereof.

12. A soybean plant product produced by the method of claim 11, wherein the plant product is produced from a plant having at least one cell of soybean cultivar 2564372.

13. A method of introducing a desired trait into soybean cultivar 2564372, wherein the method comprises:
  (a) crossing a 2564372 plant, wherein a sample of seed is deposited under NCMA No. 202104024, with a plant of another soybean cultivar having a desired trait to produce progeny plants;
  (b) selecting one or more progeny plants that have the desired trait to produce selected progeny plants;
  (c) crossing the selected progeny plants with the 2564372 plant to produce backcross progeny plants;
  (d) selecting for backcross progeny plants that have the desired trait; and
  (e) repeating steps (c) and (d) a sufficient number of times in succession to produce selected second or higher backcross progeny plants that comprise the desired trait and all of the physiological and morphological characteristics of soybean cultivar 2564372.

14. A soybean plant produced by the method of claim 13 wherein the plant has the desired trait.

15. A method for developing a soybean plant, comprising applying plant breeding techniques to the plant of claim 1, or plant part thereof, comprising crossing, recurrent selection, mutation breeding, wherein said mutation breeding selects for a mutation that is spontaneous or artificially induced, backcrossing, genomic selection, pedigree breeding, marker enhanced selection, haploid/double haploid production, or transformation, wherein application of said techniques results in development of a new soybean plant.

16. A method of introducing a mutation into the genome of soybean cultivar 2564372, said method comprising mutagenesis of the plant of claim 1, or a part thereof.

17. A method of editing the genome of soybean cultivar 2564372, said method comprising editing the genome of the plant, of claim 1, or plant part thereof, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system.

18. A soybean plant produced by the method of claim 17.

19. The seed, or part thereof, of claim 1, wherein the seed further comprises at least one seed treatment.

20. A method of creating a food or feed composition comprising extracting protein derived from the seed or part of the seed of claim 1 and adding a portion of the extracted protein to the food or feed composition.

* * * * *